United States Patent [19]

Ballis

[11] 3,968,802
[45] July 13, 1976

[54] CAUTERY PROTECTION CIRCUIT FOR A HEART PACEMAKER

[75] Inventor: Joseph A. Ballis, Roseville, Minn.

[73] Assignee: Medtronic, Inc., Minneapolis, Minn.

[22] Filed: Jan. 24, 1975

[21] Appl. No.: 543,978

[52] U.S. Cl. .................... 128/419 PG; 128/2.1 P
[51] Int. Cl.² ................................... A61N 1/36
[58] Field of Search ...... 128/419 P, 419 PG, 419 R, 128/421, 422, 423, 2.1 P; 317/9 AC, 31, 33 VR, 33 R, 43, 61.5; 331/62; 328/8; 307/262, 92

[56] References Cited
UNITED STATES PATENTS

| | | | |
|---|---|---|---|
| 3,265,956 | 8/1966 | Schlabach | 317/33 VR |
| 3,518,986 | 7/1970 | Woods et al. | 128/2.1 P |
| 3,529,211 | 9/1970 | Brayley | 317/31 |
| 3,548,294 | 12/1970 | Houghton | 317/33 VR |
| 3,587,562 | 6/1971 | Williams | 128/2.1 P |
| 3,590,322 | 6/1971 | Carr | 128/2.1 P |
| 3,768,486 | 10/1973 | Berkovits et al. | 128/419 PG |
| 3,789,854 | 2/1974 | Lee | 128/419 PG |

*Primary Examiner*—William E. Kamm
*Attorney, Agent, or Firm*—Cameron, Kerkam, Sutton, Stowell & Stowell

[57] ABSTRACT

A cautery protection circuit is disclosed for use with a heart pacemaker and comprises circuit elements for preventing those signals induced within the output portion of the heart pacemaker circuit by an electric field established by cautery procedures, from being rendered unsymmetrical in wave form, thereby minimizing the possible adverse effects of such induced signals, e.g. fibrillation of the patient's heart. In one embodiment, a diode is disposed from the emitter to the collector of a pacemaker output transistor to offset the unsymmetrical conduction of the output transistor. In another embodiment, a capacitor of a value presenting an effective short circuit to the frequencies of interest, is inserted across the output transistor to shunt thereabout signals induced by cautery procedures. In addition, the cautery protection circuit includes a suitable inductive element to reduce the high frequency current flow to the pacemaker electrodes to a level below that at which the patient's heart may be excited and further, a capacitor to detune the resonant circuit established by the capacitances of the diodes and the transistor junction, and the inductive element, from the frequencies of interest.

10 Claims, 9 Drawing Figures

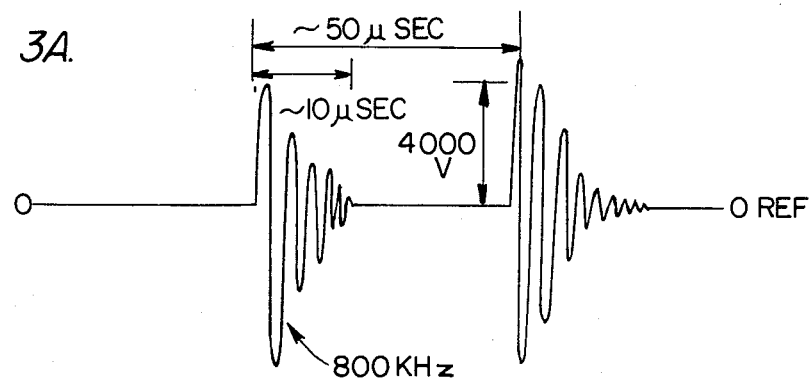
FIG. 3A.
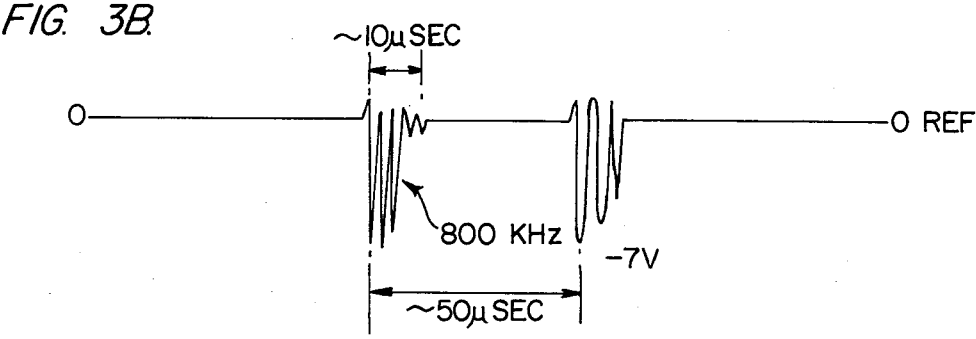
FIG. 3B.
FIG. 3C.
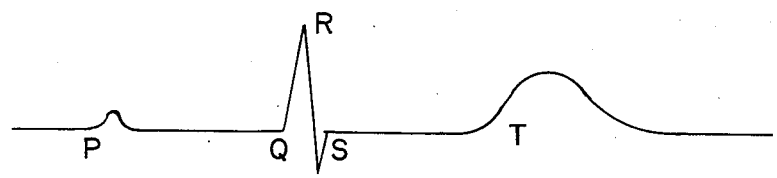
FIG. 3D.
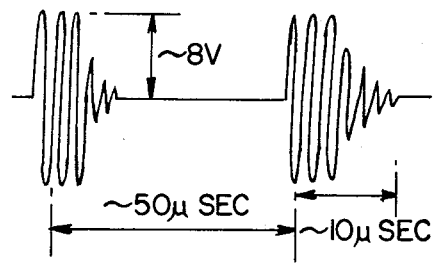

CAUTERY PROTECTION CIRCUIT FOR A HEART PACEMAKER

BACKGROUND OF THE INVENTION

1. Field of the Invention

This invention relates to electronic heart pacing apparatus and in particular to cautery protection circuits associated therewith.

2. State of The Prior Art

Heart pacers such as that described in U.S. Pat. No. 3,057,356 issued in the name of Wilson Greatbatch and assigned to the assignee of this invention, are known for providing electrical stimulus to the heart whereby it is contracted at a desired rate in the order of 72 beats per minute. Such a heart pacemaker is capable of being implanted within the human body and operative in such an environment for long periods of time. Typically, such pacemakers are implanted in the pectorial region or in the abdominal region of the patient by a surgical procedure, whereby an incision is made in such region and the pacemaker with its own internal power supply, is inserted within the patient's body.

In FIG. 1, there is shown an output portion of an electronic heart pacemaker of the prior art. The output circuitry includes a transistor Q'12 which is periodically turned on and off at a rate corresponding to that with which the patient's heart is to be stimulated, e.g. 72 beats per minute, and for a duration sufficient to stimulate the patient's heart. The base and collector electrodes are connected respectively to suitable biasing resistor R'19, and capacitor C'8 and charging resistor R'20, and the output is coupled from the collector of the transistor Q'12 by a suitable capacitor C'8. A zener diode CR'10 is connected across the output of the circuit to provide defibrillation protection. In the normal functioning of the heart, an electrical charge is established across the muscle tissue of the heart, i.e. polarization, and is subsequently discharged, i.e., depolarization. In fibrillation, there are many origins of depolarization which interact with each other and, as a result, the heart assumes a random motion, whereby little if any blood is circulated in the arterial system of the patient. To reinitiate the normal activity of the heart, a defibrillation pulse of relatively large amplitude is applied across the patient's heart. Typically, a pair of paddles (electrodes) is placed on each side of the patient's chest, whereby the defibrillation pulse is applied to his heart to reinitiate the normal rhythmic operation of his heart. The defibrillation pulse as seen by the output portion of the heart pacemaker circuit is in the order of 1500V. It is expected that such a large voltage could easily damage if not destroy the circuit elements of the circuit unless otherwise protected. To prevent this, the zener diode CR'10 is inserted across the output, thereby limiting the voltage applied to the pacemaker circuitry to a safe level, e.g. 8V.

The surgical procedure for implanting or removing the heart pacemaker into the body of the patient may involve cauterizing the incision made for the pacemaker pocket, thereby sealing off the small blood vessels surrounding the pocket. In FIG. 2, there is shown a patient with a heart pacemaker 10 implanted therein and the use of a cautery electrode 12 for cauterizing the pacemaker incision. Typically, a cautery unit such as the Bovie Electrosurgical Unit applies an electrical signal such as shown in FIG. 3A to the electrode 12. The high frequency signal has a "damped" waveform; the term damped means that the current is in pulses which start with a maximum amplitude and decrease in amplitude at a logrithmic rate. These groups of pulses are sometimes referrred to as wave trains and the number of these wave trains occurring per second is called the wave train frequency. The rate at which the pulses occur in each wave train (the number per second) denotes the frequency of the unit, e.g. 500 to 800 kilocycles per second. In the following table, I show values for several characteristics of the two basic currents. The values are approximate, but at the same time representative of current practice.

| CURRENT | OSCILLATING FREQUENCY | WAVE TRAIN FREQUENCY | PEAK OUTPUT VOLTAGE (NO LOAD) | MAXIMUM OUTPUT |
|---|---|---|---|---|
| Cutting | 500–800 KHz | 30000–50000/sec | 3000–3500 volts | 250 watts |
| Coagulating | 500–800 KHz | 10000–15000/sec | 5000–7500 volts | 150 watts |

As shown in FIG. 2, an electric field 18 is established between the cautery electrode or forcep 12 and a cautery ground plate 16 disposed against the patient's buttocks. As shown in FIG. 2, the artificial heart pulse generator 10 and its electrode 14 are disposed in the path of the field 18, whereby a signal is readily induced into the output portion of the heart pacemaker circuitry.

Through experimentation with canines, it is known that serious problems occur, not necessarily if such cautery electric field inhibits the pulse generator for a brief moment, but rather if certain extraneous signals are induced into the output portion of the heart pulse generator circuitry. In a further distinct effort, I have discovered in the course of experimentation that if an unsymmetrical waveform, as shown in FIG. 3B, is induced into the output portion of the heart pacemaker circuitry, as shown in FIG. 1, and applied by the pacemaker electrodes to the heart, the heart may be induced into fibrillation.

As can be understood with regard to FIG. 1, the signal induced into the output section of the heart pacemaker circuitry by the intense field established by cautery, is rectified by the diode CR'10 to produce the unsymmetrical wave as shown in FIG. 3B. My tests have revealed that such unsymmetrical waveforms are particularly effective, as compared with symmetrical waveforms, to stimulate the heart and thereby induce fibrillation into the heart, whereby the normal, rhythmic polarization and depolarization of the heart is interrrupted and it begins to vibrate in a relatively uncontrolled fashion.

In the normal operation of the heart, a negative charge is established upon the exterior wall of the heart muscle cells, whereas a positive charge is established therein. Then, as a spontaneous depolarization occurs, whereby the positive and negative charges appear to move toward each other, the heart cells quickly contract, the polarization dissipates, and the cells expand and repolarize more slowly. Coordination of the rhythmic polarization and depolarization of the heart muscle cells is effected by the heart's own pacemaker cells and the heart functions of rhythmically pump blood throughout the arterial system. Though the mechanism for inducing the heart into fibrillation is not completely understood, it is possible that a coincidence between the noted unsymmetrical wave and the repolarization of the heart muscle cells may be particularly effective to induce the heart into fibrillation.

The cautery procedures described above are particularly prone to induce unsymmetrical signals upon the output circuit of unipolar-type heart pacemakers. In particular, such pacemakers include a first or stimulator electrode disposed through a vein into the patient's ventricle, and a second or indifferent electrode disposed adjacent to the pacemaker. During the implantation or removal procedures, the cautery forcep may be applied to the incision leading to the pacemaker pocket within the patient. Thus, due to the proximity of the cautery electrode and the pacemaker housing, and in particular the indifferent electrode, the amplitude of the unsymmetrical signal appearing in the output portion of the heart pacemaker circuitry is particularly high. Thus, in cauterizing the incision after the heart pacemaker has been installed or before it is removed, the cautery forceps are brought very close, if not in contact with the housing of the pacemaker, thus presenting a very real problem in the induction of the undesired, unsymmetrical signal in its output circuitry.

In U.S. Pat. No. 3,757,791, there is disclosed an artificial heart pacemaker incorporating distinct atrial and ventricular pulsing circuits synchronized with each other. In the output section of each such pulsing circuit, there is incorporated a pair of zener diodes coupled in series to each other in opposing fashion to safeguard their respective circuits from excessive signals appearing across the output electrodes from an external source. In particular, there is disclosed that if defibrillation equipment is used, very high voltage may be applied to the patient's heart and that such zener diodes are incorporated to protect the pacemaker circuitry and to short-circuit the large voltage signals therethrough. The noted patent does not disclose any relationship between the described defibrillation protection circuit and the problems occurring during cautery procedures, whereby unsymmetrical signals may be applied to the heart and, in particular, there is no teaching that the defibrillation protection measures are related to shaping the cautery-induced signals.

SUMMARY OF THE INVENTION

It is therefore an object of this invention to minimize those adverse effects of signals induced into a heart pacemaker circuitry by cautery procedures.

It is a more particular object of this invention to render the cautery-induced signals into the output portion of a heart pacemaker circuitry symmetrical in character.

It is a still further object of this invention to incorporate difibrillation protection into the output circuitry of a heart pacemaker, while rendering symmetrical and reducing the amplitude of the cautery-induced wave into its output portion.

In accordance with the teachings of my invention, means are disposed within the output portion of a heart pacemaker circuit for preventing the signals induced therein due to the presence of a cautery-induced field from being rendered unsymmetrical. In one particular embodiment, the output circuitry of my heart pacemaker circuit includes an output transistor having different conductions in a first or forward direction and in a second or reverse direction, tending to render a signal induced therein symmetrical, and a diode is disposed across the output transistor in a manner to offset the unsymmetrical nature of operation of the output transistor, thereby tending to render the pacemaker conduction of cautery signals symmetrical. In a further embodiment of this invention, a capacitor of a value selcted to be a low impedance path to the frequencies of interest, is disposed across the output transistor, where the cautery-induced signals are prevented from being rendered unsymmetrical by the output transistor.

In a further aspect of this invention, the amplitude of the cautery-induced signals is reduced to a safe level by the addition of further circuit elements, e.g. an inductance inserted in the output portion of the heart pacemaker circuit in order to reduce the current flow of the high frequency components to the pacemaker stimulating electrode. In addition, a detuning capacitive element is inserted in the output circuit to detune the resonant circuit formed by the junction capacitances of the aforementioned diodes and of the output transistor, and the aforementioned inductance, a frequency offset from that of the cautery-induced signal.

In a further aspect of this invention, a second diode is disposed across the output to protect the heart pacemaker circuitry from relatively large defibrillation pulses induced therein, and a third diode is disposed in series therewith in an opposite direction to insure that cautery-induced signals are not shaped into an unsymmetrical waveform.

As a result, the pacemaker circuit of this invention insures that signals induced therein as by cautery procedures are rendered substantially symmetrical and further that such induced signals are of relatively low amplitude, thereby preventing such induced signals from driving the patient's heart into fibrillation.

BRIEF DESCRIPTION OF THE DRAWINGS

These and other objects and advantages of the present invention will become more apparent by referring to the following detailed description and accompanying drawings, in which:

FIG. 3A, 3B, 3C and 3D are, respectively, the waveforms of the output of a typical cautery unit, an unsymmetrical signal as shaped or formed by the output circuit of FIG. 1, a typical waveform of a heart beat, and a symmetrical waveform of the output of the cautery unit appearing at the pacemaker output circuit in accordance with teachings of this invention;

DESCRIPTION OF THE PREFERRED EMBODIMENTS

Figure 1:
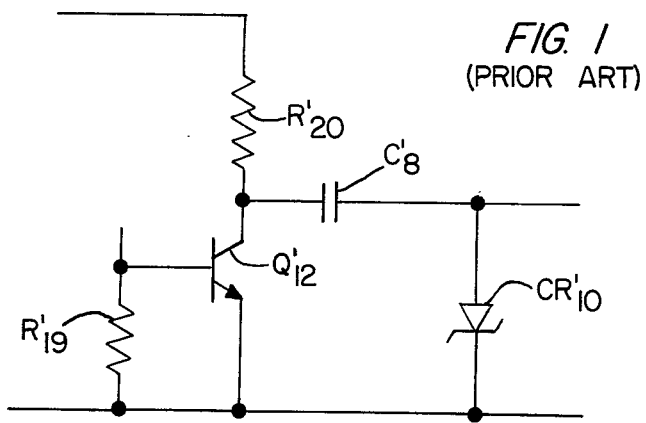
FIG. 1 is a schematic diagram of the output portion of a pacemaker circuit of the prior art.
Figure 2:
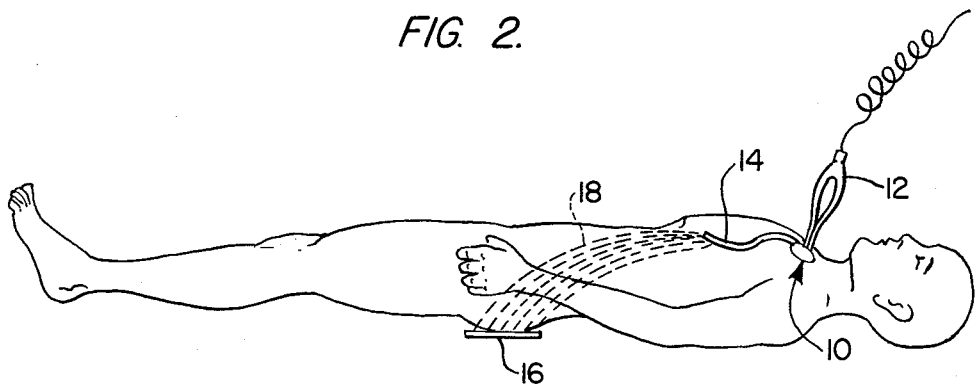
FIG. 2 is an illustration of the relative position of a cautery electrode with respect to a pacemaker pulse generator and lead implanted within a patient.
Figure 4:
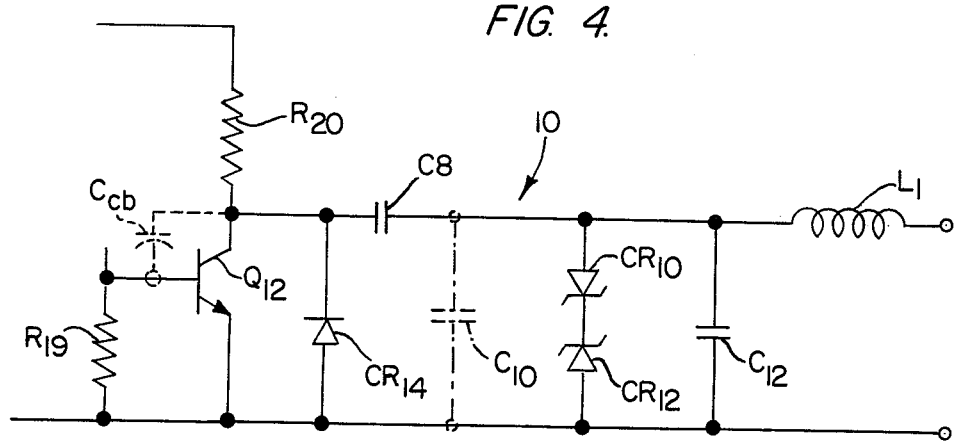
FIG. 4 is a schematic diagram of the output circuit portion of a pacemaker pulse generator circuit in accordance with teachings of this invention.

Referring now to the drawings and in particular to FIG. 4, there is shown an output portion of a pacemaker circuit 10 in accordance with the teachings of this invention. In the presence of an electric field as established between the cautery electrode or forcep 12 and the ground plate 16, as shown in FIG. 2, a signal is induced across the pair of oppositely-disposed diodes CR10 and CR12. The induced signal alternates from one polarity to the opposite whereby the diodes CR10 and CR12 rectify the alternating signal in both directions to provide a symmetrical output signal as shown in FIG. 3D. In this manner, the unsymmetrical nature of the signal, as shown in FIG. 3A, resulting from the incorporation of but a single diode in the output portion of a pacemaker circuit (as in the prior art circuit of FIG. 1) is prevented. Generally, as will be explained, the pacemaker circuit provides an energizing signal to the base of the output transistor Q12 whereby it is selectively turned on and off to apply pulses of a suitable magnitude and at a rate corresponding to that of the desired heart beat.

A second cause of the unsymmetrical nature of the cautery-induced signal appearing at the output of the heart pacemaker circuit is that conduction in the output transistor Q12 is unsymmetrical. Typically, transistor Q12 exhibits a reverse current gain $\beta_r$, lower than its forward gain $\beta_f$ and an effective collector-to-base junction capacitance $C_{cb}$ shown in dotted line in FIG. 4. The junction capacitance $C_{cb}$ of transistor Q12 serves as a current path, to the base of transistor Q12, for cautery. Thus, during the positive excursion of the cautery signal, the current is conducted through the collector-to-base junction capacitance $C_{cb}$, through resistor R19 and through the base-to-emitter junction of transistor Q12, turning transistor on in the forward direction. During the negative excursion, the current is conducted through resistor R19, collector-to-base junction capacitance $C_{cb}$ and the base-to-collector junction of transistor Q12, turning Q12 on in the reverse direction. The current passing through the base-to-collector causes an excess charge to be stored in the base of transistor Q12, effectively increasing its capacitance $C_{cb}$ which improves the current path to the base to the next positive excursion of cautery. The conduction of the cautery signal is unsymmetrical due to the difference in the $\beta_f$ and $\beta_r$ of transistor Q12, the reverse conduction being typically much lower than the forward conduction. To minimize the effect of unequal conduction in forward and reverse directions, the diode CR14 is disposed as shown in FIG. 4 to offset the greater conductance in the forward direction. As a result, the conduction, by the pacemaker output circuit, of cautery signals is made more symmetrical without reducing the amplitude of the output.

The signal as developed across the oppositely-coupled diodes CR10 and CR12 is shown in FIG. 3D. The current level of such a signal may be of sufficient amplitude to excite the heart into fibrillation. More specifically, the heart is considered to be current-sensitive as opposed to being votage-sensitive in that various voltage drops occur across the pacemaker electrodes dependent upon their construction, thereby making it difficult to accurately measure the voltage imparted to the heart; therefore, most measurements of signals applied to the heart are made in terms of current which is more easily measurable. In order to provide further protection, it is desired to reduce the current level of the signal applied to the heart, and this is accomplished by inserting an inductance L1 in the output circuit portion shown in FIG. 4 to act as a high impedance to the relatively high frequency signals of current used in cautery units. For example, the signals of spark-gap cautery units range from 500 to 800 KHz, and the inductance L1 is selected in value to limit the amplitude of signals in excess of 500 KHz. As a result, even if the cautery electrode or forcep 12 is placed very close to the indifferent electrode of the pacemaker 10, the induced cautery current is limited by the inductance L1 to prevent cardiac runaway or fibrillation.

A lumped junction capacitance C10, shown in FIG. 4 in dotted line, is illustrated as being indicative of the anode-to-cathode capacitances of the diodes CR10, CR12 and CR14 and the collector-to-emitter junction capacitance of transistor Q12. These capacitances form a tuned circuit with the added, current limiting inductance L1. In particular, the equivalent capacitance C10 is in the order of 100 picofarads while the inductance L1 takes a value of 470 $\mu$H which forms a tuned circuit at the frequencies of interest, e.g. in the order of 734 KHz. In order to detune this circuit, a further capacitance C12, having a value of 10,000 picofarads, is connected across the output whereby the tuned circuit is detuned, for the illustrative values given, to a frequency in the order of 73.4 KHz. sufficiently remote from the frequency range of interest to attenuate significantly this undesired signal being applied to the pacemaker electrodes.

Figure 5A:
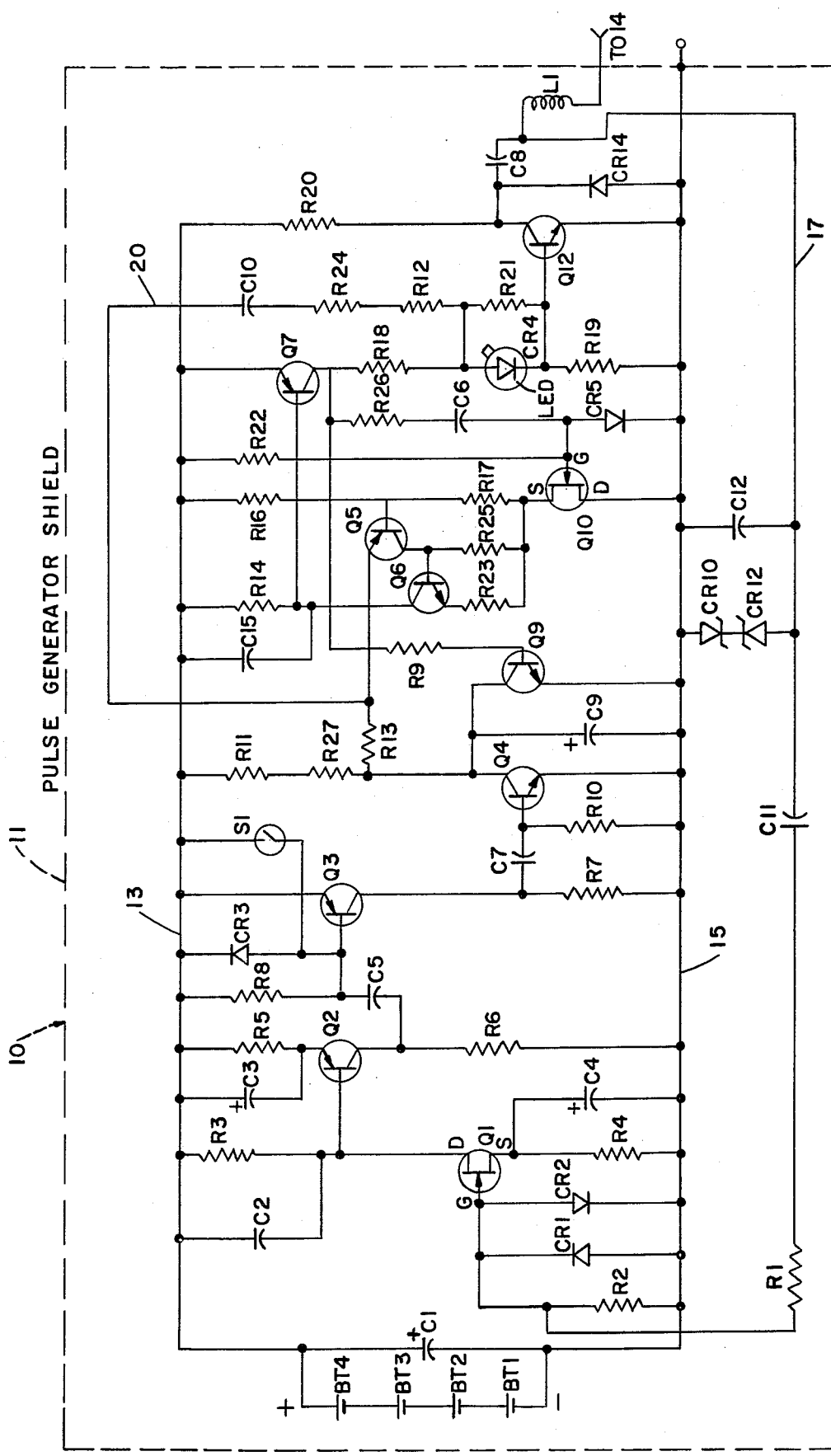
FIGS. 5A and B are a detailed schematic diagram of the entire pacemaker pulse generator circuit incorporating the output circuit portion of this invention for rendering symmetrical any signals induced by cautery and an alternative embodiment thereof, respectively.

Referring now to FIG. 5A, there is shown a schematic of a complete diagram of an illustrative embodiment heart pacemaker pulse generator circuit incorporating the cautery protection as described above with respect to FIG. 4. The heart pacemaker circuitry 10 is enclosed within a shield 11, which, in this illustrative embodiment, forms the circuit's indifferent electrode in a manner well-known in the art. The circuit 10 is energized by a source comprised of a plurality of series-connected cells BT1 to BT4, coupled collectively in parallel with a capacitor C1 and applying a positive potential to a bus 13 and a negative potential to a bus 15. The pacemaker circuitry 10 is of the demand type and responds to the heart's "R" wave derived from the stimulator electrode and applied through the lead 14, the current limiting inductor L1 and the conductor 17, indicative of the contracton of the ventricle of the heart. Generally, the R wave is sensed and if above a predetermined amplitude, inhibits the generation of the pulse by the pacemaker circuit 10 to permit the heart to continue its normal operation without the assistance of the pacemaker.

In particular, the R wave is applied through a filter circuit comprised of capacitor C11, resistor R1 and resistor R2 to the gate electrode of an FET Q1. The sensing circuit and in particular the FET Q1 is protected by a pair of oppositely-coupled diodes CR1 and CR2 which serve to limit the amplitude of the signal applied to the gate of the FET Q1. The amplified output of FET Q1 is in turn applied to the base of transistor Q2 for a second stage of amplification. Capacitor C5, connected in series with resistors R6 and R8 across buses 13 and 15, is normally charged. When transistor Q2 is rendered more or less conductive by the greater conduction or lower conduction of FET Q1, the voltage on capacitor C5 changes accordingly. If the sensed amplitude of the heart signal is above a predetermined level, e.g. ±3mV, the charge on capacitor C5 is altered to a voltage sufficient to turn normally non-conducting transistor Q3 on. The sensing and amplifying circuit of FIG. 5 is responsive to positive and negative heart signals. In particular, if a heart signal of a polarity is present to produce a drop in potential upon the collector of transistor Q2, a current will be drawn through the emitter-to-base path of transistor Q3 and capacitor C5, whereby transistor Q3 is turned on. On the other hand, if a heart signal of an opposite polarity is placed upon the input of the sensing and amplifying circuit, and increase in potential appears upon the collector of transistor Q2, thereby tending to turn transistor Q3 off and discharge C5. However, when the potential at the collector of transistor Q2 returns to its normal quiesent voltage, capacitor C5 recharges through the emitter-to-base path of transistor Q3, whereby transistor Q3 is turned on at that time.

A magnetically-actuated switch S1 is connected between the base of transistor Q3 and the positive bus 13, and serves to disable the sensing and amplifying circuit when the switch S1 is magnetically actuated. The switch S1 is inserted into the circuit to permit the doctor to disable the sensing and amplifying circuit by actuating the switch S1 with a suitable magnetic field and thereby render transistor Q3 non-conductive. With the sensing and amplifying circuit defeated, the oscillator circuit will freely oscillate and produce stimulating signals at a rate dependent on the battery voltage. Thus, the doctor may determine the operability of the pulse generator and the state of its batteries by monitoring the free-running rate and comparing the presently measured rate to the rate it exhibited at the time of implant.

Further, the collector of transistor Q3 is coupled in turn by a capacitor C7 to the base of transistor Q4. If the amplitude of the heart signal is above the predetermined level, the transistor Q3 is rendered conductive, thereby raising the voltage applied through the capacitor C7 to the base of transistor Q4 toward the potential placed upon bus 13, thereby turning transistor Q4 on. In this manner, the heart signal is amplified and sensed, and if it is above the predetermined level, transistor Q4 is rendered conductive, thereby interrupting the operation of the pulse generator to be described and resetting its timing cycle.

In FIG. 5A, there is shown a refractory circuit for providing a refractory period during which the pacemaker sensing circuit is disabled, i.e. unable to sense a heart R wave signal, for a period in the order of 300 milliseconds as initiated by the production of the pacemaker artifact at the output circuit. The refractory circuit comprises the resistor R4 and the capacitor C4 connected in parallel with each other, which combination is connected between the source of FET Q1 and the bus 15. Normally, in the absence of a sensed signal on the gate of FET Q1, FET Q1 is conductive to a certain degree and capacitor C4 is charged through resistor R3 and the drain-source channel of FET Q1 to a quiescent voltage level determined by resistor R4. Upon the application of a positive input signal to the gate of FET Q1, FET Q1 is rendered more conductive and capacitor C4 is charged to a higher voltage level than its quiescent voltage since the resistance of the drainsource channel decreases. During the refractory period, FET Q1 is not turned on due to the reverse bias placed upon its gate to source by the higher voltage level to which capacitor C4 has been charged. Upon the removal of the input signal, capacitor C4 tends to discharge through resistor R4 to its normal biased quiescent potential, at which point the reverse bias applied to the gate to source of FET Q1 is reduced, permitting it to again be turned on by another input signal at its gate. Thus, it can be seen that the values of capacitor C4 and resistor R4 are selected to provide a capacitor discharge timing period corresponding to the desired refractory period.

In the absence of the normal operation of the patient's heart as indicated by the sensed signal, a capacitor C9 is charged by current through the resistors R11 and R27 at a rate determined by the R-C time constant of the series circuit; the rate of charging of capacitor C9 in turn determines the rate at which pulses are to be applied by the heart pacemaker circuit 10 to the patient's heart. The voltage charge developed on capacitor C9 is applied through resistor R13 to the emitter of transistor Q5, and upon reaching a predetermined level in excess of the bias voltage established upon its base, transistor Q5 is rendered conductive. In turn, transistor Q5, upon being rendered conductive, raises the voltage applied to the base of transistor Q6 whereby it is also turned on. As seen in FIG. 5A, the collector of transistor Q6 is coupled to the base of transistor Q7 and upon being rendered conductive, reduces the voltage applied thereto, turning transistor Q7 on. When transistor Q7 is rendered conductive, the potential applied at the common point between its collector and resistor R18 is raised upward toward that established upon bus 13. In turn, an increased voltage is applied through resistors R18 and R21 to the base of the output transistor Q12, thereby turning it on for a pulse width period determined in a manner to be explained.

As the voltage at the collector of transistor Q7 is raised, a correspondingly more positive voltage is applied through resistor R9 to the base transistor Q9 whereby it is rendered conductive, thereby discharging capacitor C9 in preparation for the next cycle of operation of the pacemaker oscillator circuit. Further, the increased voltage is applied through resistors R18, R12 and R24 to charge capacitor C19, whereby the potential applied to the emitter of transistor Q5 decreases as capacitor C10 charges and after a predetermined interval, i.e. the pulse width of the stimulator signal, corresponding to the values of resistive elements R18, R12 and R24 and the value of capacitor C10, capacitor C10 is fully charged and transistor Q5 is turned off.

As seen in FIG. 5A, an LED CR4 is connected in series with resistive elements R18 and R19, between the collector of transistor Q7 and the bus 15. Thus, the potential applied across the resistor R21 is maintained relatively constant in spite of battery source depletion. Thus, as the transistor Q7 is rendered conductive, the voltage at the base of transistor Q12 is raised, rendering it conductive, and the charging of capacitor C10 commences, whereby a decreasing potential is applied to the emitter of transistor Q5 via conductor 20 whereby after a period of time corresponding to the pulse width of the stimulator pulse, e.g. 0.5 to 1.2 msec, the transistor Q5 is turned off. As a result, transistors Q6, Q7 and Q12 are turned off to terminate the pulse output of the pacemaker circuit 10 as derived from the transistor Q12. As transistor Q7 is rendered non-conductive, transistor Q9 is likewise rendered non-conductive, thus permitting capacitor C9 to recharge to initiate the next cycle of operation in a manner as explained above.

Further, capacitor C10 is discharged when transistor Q4 is rendered conductive upon either sensing a natural heart signal above the predetermined amplitude or when transistor Q9 is rendered conductive, whereby a conductive path is provided through resistor R13 and transistors Q4 or Q9 to the negative bus 15. Thus, capacitor C10 is prepared for the next cycle of the oscillator to be charged and to time the pulse width of the heart stimulator signal.

In FIG. 5A, the oscillator circuit includes an FET Q10 whose source is connected through resistor R17 to the base of transistor Q5 and whose drain is connected to the negative bus 15. The gate of FET Q10 is connected through resistive element R22 to the positive bus 13 and also to the point of interconnection between the diode CR5 and the capacitor C6. In turn, the diode CR5 is further connected to the negative bus 13, whereas the capacitor C6 is connected in series through resistive element R26 to the collector of transistor Q7. The FET Q10 serves to prevent the oscillator circuit from stimulating the patient's heart at too fast a rate in the event one of its elements should become defective in any manner. For example, if the resistance R16 becomes an open circuit, the transistor Q5 would turn on prematurely with the result that a very rapid, possibly dangerous series of stimulating pulses would be applied to the patient's heart. In operation, FET Q10 is normally biased to a conducting state. To terminate the pulse width of the stimulating heart pulse, transistor Q5 is rendered non-conductive in a manner as explained above, whereby transistors Q6 and Q7 are also rendered non-conductive. While transistors Q5, Q6 and Q7 are rendered conductive, capacitor C6 connected to the gate of FET Q10 is charged. When transistor Q7 is turned off, the negative charge established upon capacitor C6 serves to bias off FET Q10, thereby preventing FET Q10 from being turned on again for a period dependent upon the discharge time of capacitor C6. As shown in FIG. 5, capacitor C6 discharges primarily through resistive element R22 but also through resistive elements R18, R26, R19 and R21, the discharge time being in the order of 500 to 600 msec. While FET Q10 is rendered non-conductive, transistor Q5 and therefore transistors Q6, Q7 and Q8 may not be turned on. Thus, if one of the elements within the oscillator circuit becomes defective, thereby tending to turn transistor Q5 on prematurely, FET Q10 serves a protective function, preventing the premature conduction of the noted transistors and therefore limits the rate at which stimulating pulses may be applied to the patient's heart, to a rate in the order of 110 beats per minute.

It is understood that the pacemaker circuit 10 will continue to oscillate at a rate determined by the values of capacitor C9 and resistors R11 and R27 to produce a pulse of a width determined by the values of resistors R18, R12 and R24 and capacitor C10, until an inhibiting pulse is applied to the base of transistor Q4, whereby it is rendered conductive and capacitor C9 is discharged to terminate the operation of the pulse generating circuit. The stimulating signal applied to the patient's heart by the pacemaker lead 14 is developed by the discharge of the capacitor C8 during the conduction period of the transistor Q12 through a series path including transistor Q12, bus 15, the electrodes of pacemaker lead 14 and the patient's body, inductor L1 and capacitor C8. During the interval between stimulating signals, capacitor C8 recharges to battery potential through bus 13, load resistor R20, capacitor C8, inductor L1, the electrodes of lead 14 and the patient's body, and bus 15. The amplitude of the recharging signal is insufficient to trigger a contraction of the patient's heart muscle.

In a manner as explained above with respect to FIG. 4, a pair of diodes CR10 and CR12 is connected in series but opposite directions between the bus 15 connected to the pulse generator shield 11 forming one electrode and the lead 17 coupled to the high frequency current limiting inductance L1. Further, the unsymmetrical conduction compensating diode CR14 is connected between the emitter and the collector of transistor Q12, and the detuning capacitor C12 is connected in parallel with the diodes CR12 and CR10.

The frequency components and repetition frequency or rate of the stimulating signal differ widely from the resonant frequency of the inductor L1 and capacitor C12, so that there is no danger of resonance of the output circuit through the normal operation of the pulse generator circuit.

Figure 5B:
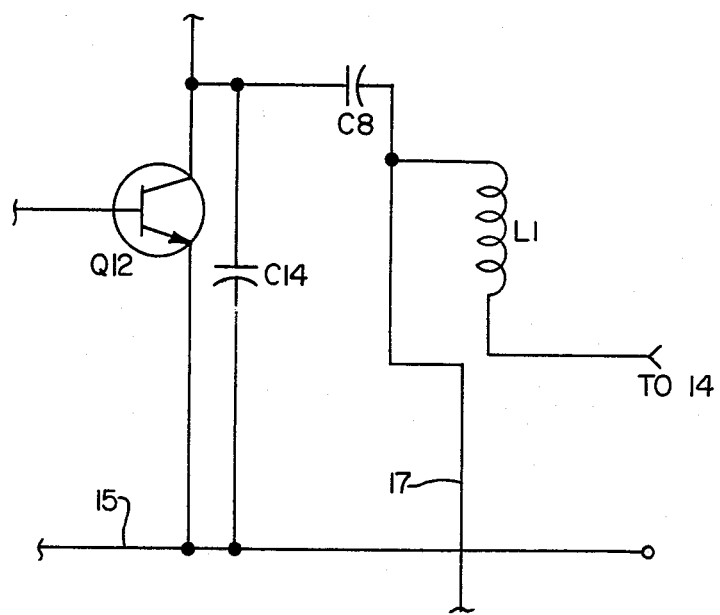

In an alternative embodiment of this invention, as shown in FIG. 5B the diode CR14 as shown in FIG. 5A may be removed and a capacitor C14 inserted in the pacemaker output circuit. The value of the capacitor C14 is selected such that it provides a low impedance path to the signals induced in the pacemaker output as by cautery procedures, whereby the induced signals are shunted or shorted about the output transistor Q12. In this manner, the transistor Q12, which has differing conductions therethrough, is not impressed with relatively large signals and therefore is prevented from rendering these signals unsymmetrical. Further, the capacitor C12, which was incorporated herein to detune the resonance circuit formed by the capacitance of transistor Q12, capacitor C8 and the inductance L1, may also be removed and its function assumed by capacitor C14.

Though the cautery protection circuit of this invention has been described as being inserted into the pacemaker circuit as shown in FIG. 5, it is understood that it may be used with other pacemaker circuits as shown in each of U.S. Pat. Nos. 3,478,746; 3,391,697; and 3,656,487, as well as other pacemaker circuits.

The cautery protection circuit as shown in FIGS. 4 and 5 has been tested with regard to the possible negative effects of cautery upon the heart. A cautery electrode or forcep has been brought within half-inch from the pulse generator shield 11 forming the indifferent electrode of the circuit 10 as shown in FIG. 5, with no dangerous stimulation of the tested hearts by the cautery signals.

Numerous changes may be made in the above-described apparatus and the different embodiments of the invention may be made without departing from the spirit thereof; therefore, it is intended that all matter contained in the foregoing description and in the accompanying drawings shall be interpreted as illustrative and not in a limiting sense.

What is claimed is:

1. A heart pacemaker circuit comprising:
   a. output switch means controllably turned on and off at a rate corresponding to that with which it is desired to stimulate a patient's heart and having outputs from which a heart stimulating signal is derived, said switch means being characterized by a first conduction therethrough greater than a second conduction in an opposite direction therethrough; and b. means disposed across the output of said switch means for preventing the difference between the first and second conductions of said switch from rendering induced signals in the circuit output unsymmetrical.

2. The circuit as claimed in claim 1, wherein said preventing means comprises a first unidirectional conduction means disposed across the output of said switch means in a manner to offset the unsymmetrical operation of said switch means due to the difference between the first and second conductions thereof.

3. The circuit as claimed in claim 2, wherein there is further inclulded second unidirectional conduction means disposed in circuit with said switch means in a first direction to prevent relatively high ampltidue signals induced therein by extraneous fields from damaging the circuit components of said heart pacemaker circuit, and third unidirectional conduction means connected in series with said second unidirectional conduction means and in a second, opposite direction across the output of said switch means, whereby the cautery induced signals in the output of said heart pacemaker circuit are substantially symmetrical in wave form.

4. The circuit as claimed in claim 3, wherein there is included inductance means coupled between one of said outputs of said heart pacemaker circuit and a heart stimulator electrode for limiting the amplitude of the currents flowing therethrough within the range of the frequencies of interest.

5. The circuit as claimed in claim 4, wherein said switch means, said first, second and third unidirectional conduction means each has a characteristic capacitance and form with said inductance means a tuned circuit resonant at a first frequency, and there is included capacitance means connected in circuit with said tuned circuit for detuning said tuned circuit to a frequency remote from said first frequency.

6. The circuit as claimed in claim 1, wherein said preventing means comprises a capacitor disposed across the output of said switch means and of a value for providing a shunt path about said switch means to signals of the frequencies of interest.

7. The circuit as claimed in claim 1, wherein said switch means comprises a transistor.

8. In a unipolar pacemaker circuit to be incorporated within a patient for stimulating his heart comprising:

a. pulse generator means including timing circuit means operable to control output pulses from said generator means at a selected frequency corresponding to the desired heart beat of the patient;

b. first electrode means coupled to said pulse generator means and forming a shield thereabout and second electrode means coupled to receive the output pulses of said pulse generator means and adapted to be electrically coupled to the patient's heart;

c. said pulse generator means comprising an output transistor having different forward and reverse gain characteristics;

d. first and second diodes connected in series with each other and in circuit from said first to said second electrode means, said first diode coupled to protect said pulse generator means from defibrillation-induced signals and said second diode coupled in an opposite direction for insuring that the output signal due to cautery induced signals appearing across said first and second electrode means is substantially symmetrical in wave form; and e. a third diode disposed in circuit from the emitter to the collector of said output transistor in a direction so as to compensate for the difference in the forward and reverse gain characteristics thereof.

9. In the unipolar pacemaker circuit as claimed in claim 8, wherein there is included an inductive element disposed in circuit with said second electrode means for attenuating high frequency currents passing therethrough.

10. In the unipolar pacemaker circuit as claimed in claim 9, wherein a resonant circuit is formed of the base-to-emitter capacitance of said output transistor and said anode-to-cathode capacitances of said first and second diodes, and of said inductive element at frequencies in the range of that induced in the output of said circuit by cautery, and there is included a capacitive element connected in circuit between said first and second electrode means to detune said resonant circuit to a frequency remote from said range.

* * * * *